United States Patent
Wohlman et al.

(10) Patent No.: US 6,891,051 B1
(45) Date of Patent: May 10, 2005

(54) SILICONE ERUCATE ESTERS

(75) Inventors: Alan Wohlman, Northbrook, IL (US); Anthony J. O'Lenick, Jr., Dacula, GA (US)

(73) Assignee: FanTech LTD, Chicago, IL (US)

( * ) Notice: Subject to any disclaimer, the term of this patent is extended or adjusted under 35 U.S.C. 154(b) by 139 days.

(21) Appl. No.: 10/425,119

(22) Filed: Apr. 29, 2003

(51) Int. Cl.$^7$ .............................................. C07F 11/00
(52) U.S. Cl. ....................................................... 554/77
(58) Field of Search ........................................... 554/77

Primary Examiner—Deborah D. Carr

(57) ABSTRACT

The invention relates to a series of novel silicone fatty esters, specifically dimethicone copolyol erucate esters. This class of compounds provides has a unique combination of properties including clarity and liquidity and oxidative stability and water solubility of the silicone ester per se, and the ability to provide outstanding softening and wet comb lubrication, as well as actually strengthening the hair. These properties are highly desirable in cosmetic products. The compounds of the present invention are prepared by reacting the hydroxyl group in a silicone polymer with erucic acid, or an oil high in erucic acid like crambe oil. The compounds of the present invention have more than 40% by weight of erucic groups in the molecule. The concentration of this key component has been found to be critical to performance.

7 Claims, No Drawings

SILICONE ERUCATE ESTERS

BACKGROUND OF THE INVENTION

The invention relates to a series of novel silicone fatty esters, specifically dimethicone copolyol erucate esters. This class of compounds provides has a unique combination of properties including clarity and liquidity and oxidative stability and water solubility of the silicone ester per se, and the ability to provide outstanding softening and wet comb lubrication when applied to hair of the product in formulated products. These properties are highly desirable in cosmetic products. Even more importantly, treatment of the hair with the compounds of the current invention actually improves the strength of the hair. The compounds of the present invention are prepared by reacting the hydroxyl group in a silicone polymer with erucic acid, or an oil high in Erucic acid like crambe oil.

FIELD OF THE INVENTION

The field of the invention relates to a series of novel silicone fatty esters, specifically dimethicone copolyol erucate esters. This class of compounds provides has a unique combination of properties including clarity and liquidity and oxidative stability and water solubility of the silicone ester per se, and the ability to provide outstanding softening and wet comb lubrication when applied to hair of the product in formulated products. These properties are highly desirable in cosmetic products. These properties are highly desirable in cosmetic products. Even more importantly, treatment of the hair with the compounds of the current invention actually improves the strength of the hair. The compounds of the present invention are prepared by reacting the hydroxyl group in a silicone polymer with erucic acid, or an oil high in Erucic acid like crambe oil.

Arts and Practices

U.S. Pat. No. 5,136,063 issued to O'Lenick in August 1992 discloses a series of silicone esters that range in carbon length from C12 to C21. The compounds are claimed to provide outstanding softening and lubricating when applied to textiles and fibers. The patent states: "It is the object of the present invention to provide novel silicone based fatty ester compounds which are substantive to the surface of a fiber and other textile materials including cellulosic material and have increased solubility in fatty materials including mineral oil, fatty triglycerides and traditional fatty quaternary ammonium compounds. The compounds of the present invention render the lubricity, and hydrophobicity generally seen in silicone compounds, but because they are esterified with fatty groups have greater solubility in hydrocarbon oils as well as fatty materials than the traditional silicone compounds, which are insoluble in those materials."

As will become clear from the teaching of the current invention, the patent U.S. Pat. No. 5,136,063 did not recognized that only by proper selection of the starting acid (Erucic acid) and the proper silicone polymer, a product could be prepared that provides unexpected properties valuable properties in personal care applications, a very different application area than the textile art to which the U.S. Pat. No. 5,136,063 patent applies. These unexpected properties include clarity and homogeneity of product per se, good water solubility, oxidative stability and the ability to provide outstanding conditioning and wet comb properties to hair in anionic systems.

OBJECT OF THE INVENTION

It is the object of the present invention to provide a series of novel silicone erucate esters, that provide a unique combination of properties including clarity and liquidity and oxidative stability and water solubility of the silicone ester per se, and the ability to provide outstanding softening and wet comb lubrication when applied to hair of the product in formulated products. The compounds of the present invention have more than 40% by weight of erucic groups in the molecule. This is achieved either using highly purified erucic acid or picking an oil that has over 40% by weight erucic in it. The concentration of this key component has been found to be critical to performance.

It is another object of the present invention to provide a process for treating hair, which comprises contacting the hair with an effective conditioning amount of a series of novel silicone erucate esters. The process provides outstanding softening and wet comb lubrication when applied to hair of the product in formulated products. The treatment of the hair with the compounds of the current invention actually improves the strength of the hair.

SUMMARY OF THE INVENTION

The invention relates to a series of novel silicone fatty esters, specifically dimethicone copolyol erucate esters. This class of compounds provides has a unique combination of properties including clarity and liquidity and oxidative stability and water solubility of the silicone ester per se, and the ability to provide outstanding softening and wet comb lubrication when applied to hair of the product in formulated products. These properties are highly desirable in cosmetic products. The compounds of the present invention are prepared by reacting the hydroxyl group in a silicone polymer with erucic acid, or an oil high in erucic acid like crambe oil. The compounds of the present invention have more than 40% by weight of erucic groups in the molecule. This is achieved either using highly purified erucic acid or picking an oil that has over 40% by weight erucic in it. The concentration of this key component has been found to be critical to performance.

DETAILED DESCRIPTION OF THE INVENTION

The compounds of this invention are silicone fatty esters made by the esterification of a dimethicone copolyol compound with erucic acid or an oil that has a high concentration of erucic acid. By high concentration of erucic acid is meant that the oil has in excess of 40% by weight erucic moieties. The compounds of the present invention conform to the following structure;

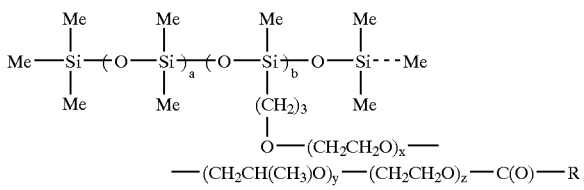

wherein;
Me is methyl;
R is $CH_3$—$(CH_2)_7$CH=CH—$(CH_2)_9$—;
a is an integer ranging from 1 to 20;
b is an integer ranging from 1 to 20;
x and z are independently integers ranging from 0 to 20;
y is an integer ranging from 5 to 20, with the proviso that x+z are greater than twice the value of y.

Another aspect of the present invention is a process for conditioning hair, which comprises contacting the hair with an effective conditioning concentration of a silicone erucate ester, which conforms to the following structure:

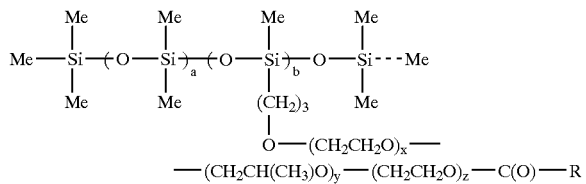

wherein;
Me is methyl;
R is $CH_3-(CH_2)_7CH=CH-(CH_2)_{11}-$;
a is an integer ranging from 1 to 20;
b is an integer ranging from 1 to 20;
y x and z are independently integers ranging from 0 to 20;
y is an integer ranging from 5 to 20, with the proviso that x+z are greater than twice the value of y.

The effective conditioning concentration ranges from 0.1% by weight to 25% by weight.

Preferred Embodiments

In a preferred embodiment the erucate is derived from erucic acid.

In a preferred embodiment the erucate is derived from crambe oil.

In a preferred embodiment x is an integer ranging from 1 to 20; y is zero and z is zero.

In a preferred embodiment x is an integer ranging from 1 to 20; y is zero and z is zero.

In a preferred embodiment x is an integer ranging from 1 to 20; y is zero and z is zero.

In a preferred embodiment x is 5, y is 0 and z is 0.

In a preferred embodiment x is 8, y is 3 and z is 2.

EXAMPLES

Erucic Acid

Erucic Acid is an item of commerce available from a variety of sources, including Uniquema and Cognis. It conforms to the following structure:

$$CH_3-(CH_2)_7CH=CH-(CH_2)_{11}-C(O)-OH$$

Erucic acid is also a major component of Carmbe oil. Crambe, whose Latin name is Crambe abyssinica, was first introduced into the United States from Europe in the 1940s by the Connecticut Agricultural Experiment Station. The composition of the triglyceride contains high levels of erucic acid, generally between 55 to 60%.

It is a unique acid in that it is a soft solid which is a major reason for its lack of rancidity and ability to provide outstanding wet comb properties to hair. Oleic acid, which is the C18 unsaturated product is a liquid that is quite prone to rancidity resulting in mal odor. Oleic derivatives give a "cheesy" feel on the hair and no improvement in wet comb.

Crambe Oil

Crambe is a cool-season oilseed that grows best in semi-arid regions with warm days, cool nights, and low humidity. The crop is grown for its oil, which contains high amounts of Erucic acid, a 22-carbon fatty acid.

Crambe oil has the following typical properties:

| Melting point | 6° C. |
|---|---|
| Iodine Value | 93 mg KOH/gram |
| Saponification Value | 160–175 mg KOH/gram |
| Typical Erucic Content | 55%–60% by weight |

Dimethicone Copolyols

Dimethicone copolyols are also called silicone glycols, and silicone surfactants. They are available form a variety of manufacturers. Siltech Corporation of Toronto Ontario Canada is a major one.

They conform to the following structure:

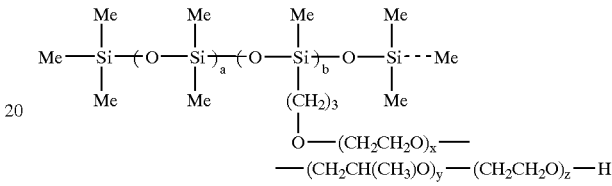

wherein;
Me is methyl;
a is an integer ranging from 1 to 20;
b is an integer ranging from 1 to 20;
x and z are independently integers ranging from 0 to 20;
y is an integer ranging from 5 to 20, with the proviso that x+z are greater than twice the value of y.

Examples 1–10

| Example | a | b | x | y | z | Molecular Weight | % Water Soluble |
|---|---|---|---|---|---|---|---|
| 1 | 1 | 10 | 5 | 0 | 0 | 795 | 55 |
| 2 | 5 | 4 | 5 | 1 | 5 | 2,702 | 65 |
| 3 | 10 | 10 | 8 | 3 | 2 | 8,244 | 53 |
| 4 | 5 | 6 | 20 | 0 | 20 | 19,748 | 89 |
| 5 | 20 | 7 | 20 | 20 | 20 | 23,487 | 52 |
| 6 | 15 | 20 | 8 | 1 | 0 | 12,278 | 57 |
| 7 | 9 | 4 | 8 | 0 | 0 | 4,681 | 68 |
| 8 | 10 | 10 | 0 | 7 | 14 | 12,364 | 50 |
| 9 | 20 | 10 | 5 | 5 | 5 | 10,160 | 43 |
| 10 | 9 | 5 | 3 | 1 | 5 | 3,030 | 51 |

General Reaction Conditions;

The esterification can be carried out without catalyst; however, when no catalysts are used reaction rates are less efficient. Standard esterification catalysts are generally used at concentrations of between 0.05% to 0.50% with a preferred range of 0.1% to 0.3%. Catalysts which are effective include but are not limited to; sulfuric acid, p-toluene sulfonic acid, methane sulfonic acid, tin metal, zinc metal, titanium metal, organo titianates, organo tin compounds, organo zinc compounds, zinc oxide, magnesium oxide, calcium oxide, etc. The most preferred catalyst is stannous oxylate. The reaction is conducted at between 140 and 240 C under an inert nitrogen blanket. The nitrogen blanket to preserves the color. Preferred temperature range is between 180 and 210 C. Water is removed from the reaction, which is done using a nitrogen sparge or vacuum.

The reaction can be run with either a stoichiometric amount of the erucic acid, or a slight excess of either reactant.

Ester Examples

Example 11

Into a suitable round bottom, three neck flask equipped with a Dean Stark trap, a thermometer and a nitrogen sparge is added 330.0 grams of erucic acid, 0.25% by weight of the total batch charged of stannous oxylate and 795.0 grams of dimethicone copolyol (example 1). The reaction mass is blanketed with nitrogen, and heated to 180 and 200 C under an inert nitrogen blanket. Once the reaction temperature reaches 120 C water begins to boil off and is collected in the Dean Stark Trap. Within four to five hours the theoretical water is collected off and the acid value is very low. The product is a clear liquid and is used without additional purification.

Examples 12

Example 11 is repeated only this time substituting the specified number of grams of the specified dimethicone copolyol.

|  | Silicone Compound |  |
| --- | --- | --- |
| Example | Example | Grams |
| 12 | 2 | 2,702 |
| 13 | 3 | 8,244 |
| 14 | 4 | 19,748 |
| 15 | 5 | 23,487 |
| 16 | 6 | 12,278 |
| 17 | 7 | 4,681 |
| 18 | 8 | 12,364 |
| 19 | 9 | 10,160 |
| 20 | 10 | 3,030 |

Transesterification Examples

Example 21

Into a suitable round bottom, three neck flask equipped with a Dean Stark trap, a thermometer and a nitrogen sparge is added 330.0 grams of crambe oil, 0.25% by weight of the total batch charged of stannous oxylate and 795.0 grams of dimethicone copolyol (example 1). The reaction mass is blanketed with nitrogen, and heated to 180 and 200 C under an inert nitrogen blanket. Once the reaction temperature reaches 120 C water begins to boil off and is collected in the Dean Stark Trap. Within four to five hours the theoretical water is collected off and the acid value is very low. The product is a clear liquid and is used without additional purification.

Examples 22

Example 21 is repeated only this time substituting the specified number of grams of the specified dimethicone copolyol.

|  | Silicone Compound |  |
| --- | --- | --- |
| Example | Example | Grams |
| 22 | 2 | 2,702 |
| 23 | 3 | 8,244 |
| 24 | 4 | 19,748 |
| 25 | 5 | 23,487 |
| 26 | 6 | 12,278 |
| 27 | 7 | 4,681 |
| 28 | 8 | 12,364 |
| 29 | 9 | 10,160 |
| 30 | 10 | 3,030 |

Applications Examples

In order to show the effectiveness of the compositions of the present invention as conditioners on hair and skin the following formula was evaluated;

Shampoo Formula

| Material | % |
| --- | --- |
| Water | 37.9 |
| Disodium EDTA | 0.1 |
| Sodium Laureth-2-sulfate | 45.0 |
| Cocamidopropyl betaine | 8.0 |
| Cocamide MEA | 3.0 |
| Composition Example | 5.0 |
| NaCl | 1.0 |

The hair conditioning was evaluated using half head salon tests and a scale from 1–5 (with 5 being excellent) was used. The following shows the results:

| [040] Ester Example | Evaluation |
| --- | --- |
| 13 | 5 |
| 10 | 4 |
| 23 | 4 |
| 30 | 5 |

Example not of the present invention

Example 12

Hair Strengthening
Protocol

Unprocessed Caucasian hair swatches were purchased from DeMao Brothers. They were prepared to be equal weight. A 3% aqueous solution of the specified examples was prepared. A hair swatch was submerged in the test solution at 37° C. for 10 minutes and allowed to air dry at room temperature. Individual fibers were chosen from each and tested using a "Dai-Stron Tensile Tester".

Example

| Ester Example | Break Load (gm) |
| --- | --- |
| 13 | 110 |
| 10 | 115 |
| 23 | 111 |
| 30 | 116 |

Example not of the present invention

| Test Material | Break Load (gm) |
|---|---|
| Example 1 | 80 |
| Water | 76 |

The above data clearly shows that hair treated with the compounds of the present invention have improved strength as tested with the amount of weight needed per unit area to break the fiber. Improving the strength of the hair is a very important attribute for cosmetic products in that it minimizes hair loss and improves hair's ability to be treated and combed.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A silicone erucate ester, which conforms to the following structure:

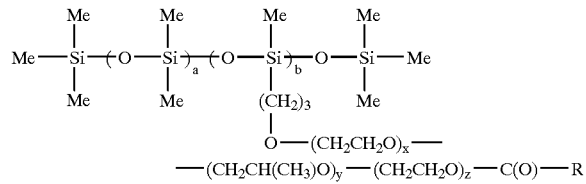

wherein:

Me is methyl;

R is $CH_3-(CH_2)_7CH-CH-(CH_2)_{11}$;

a is an integer ranging from 1 to 20;

b is an integer ranging from 1 to 20);

x and z are independently integers ranging from 0 to 20;

y is an integer ranging from 5 to 20, with the proviso that x+z are greater than twice the value of y.

2. A silicone erucate ester of claim 1 wherein the erucate is derived from crucic acid.

3. A silicone crucate ester of claim 1 wherein the crucate is derived from crambe oil.

4. A process for conditioning hair, which comprises contacting the hair with an effective conditioning concentration of a silicone erucate ester, which conforms to the following structure:

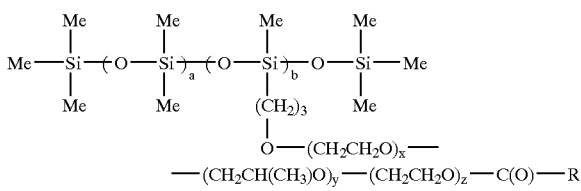

wherein;

Me is methyl;

R is $CH_3-(CH_2)_7CH=CH-(CH_2)_{11}-$;

a is an integer ranging from 1 to 20;

b is an integer ranging from 1 to 20;

x and z are independently integers ranging from 0 to 20;

y is an integer ranging from 5 to 20, with the proviso that x+z are greater than twice the value of y.

5. A process of claim 4 wherein said effective conditioning concentration ranges from 0.1% by weight to 25% by weight.

6. A process of claim 5 wherein the crucate is derived from crucic acid.

7. A process of claim 5 wherein the erucate is derived from crambe oil.

* * * * *